(12) United States Patent
Firmbach et al.

(10) Patent No.: US 12,402,892 B2
(45) Date of Patent: Sep. 2, 2025

(54) SURGICAL INSTRUMENT

(71) Applicant: Aesculap AG, Tuttlingen (DE)

(72) Inventors: Franz-Peter Firmbach, Emmingen-Liptingen (DE); Svenja Anhorn, Heroldstatt (DE)

(73) Assignee: Aesculap AG, Tuttlingen (DE)

( * ) Notice: Subject to any disclaimer, the term of this patent is extended or adjusted under 35 U.S.C. 154(b) by 318 days.

(21) Appl. No.: 18/321,912

(22) Filed: May 23, 2023

(65) Prior Publication Data

US 2023/0380844 A1 Nov. 30, 2023

(30) Foreign Application Priority Data

May 24, 2022 (DE) ...................... 10 2022 205 194.7

(51) Int. Cl.
*A61B 17/15* (2006.01)
*A61B 17/16* (2006.01)
*A61F 2/46* (2006.01)

(52) U.S. Cl.
CPC ........ *A61B 17/155* (2013.01); *A61B 17/1659* (2013.01); *A61F 2/4657* (2013.01)

(58) Field of Classification Search
CPC ........................ A61B 17/155; A61B 17/154
See application file for complete search history.

(56) References Cited

U.S. PATENT DOCUMENTS

| | | | |
|---|---|---|---|
| 5,364,401 | A | 11/1994 | Ferrante et al. |
| 6,056,756 | A | 5/2000 | Eng et al. |
| 2017/0100132 | A1 | 4/2017 | Collazo |

FOREIGN PATENT DOCUMENTS

| | | |
|---|---|---|
| DE | 69324233 T2 | 12/1999 |
| DE | 60308475 T2 | 6/2007 |
| EP | 1543784 A2 | 6/2005 |

*Primary Examiner* — Andrew Yang
(74) *Attorney, Agent, or Firm* — Christopher A. Rothe; CM Law (57) ABSTRACT

A surgical instrument and surgical instrument system for use in a knee replacement operation. The surgical instrument includes a fastening device configured for direct or indirect releasable fastening to a cutting block for the distal resection of a femur, a sensing device with a posteriorly oriented reference plane configured to bear against an anterior surface of the femur, and a bearing device for positioning the reference plane. The bearing device includes at least one pivoting bearing with an anteroposteriorly oriented pivot axis, about which the reference plane can be moved pivotably relative to the fastening device.

12 Claims, 7 Drawing Sheets

SURGICAL INSTRUMENT

CROSS-REFERENCE TO RELATED APPLICATION(S)

This application claims priority under 35 U.S.C. § 119 to German Application No. 10 2022 205 194.7, filed May 24, 2022, the content of which is incorporated by reference herein in its entirety.

FIELD

The present disclosure relates to a surgical instrument for use in a knee replacement operation.

BACKGROUND

The use of orthopaedic prostheses as an artificial replacement for damaged or worn natural bone structures is common medical practice. In particular, hip and knee replacement operations belong in the meantime to the standard repertoire of surgical orthopaedics.

In a knee replacement operation (Total Knee Arthroplasty (TKA)), joint surfaces of the femur and/or the tibia which are worn or impaired by illness or an accident are replaced by a knee prosthesis. Knee prostheses of this type usually comprise a femoral component which is implanted at the distal end of the femur and a tibial component which is implanted at the proximal end of the tibia. In order to ensure a proper function of the artificial joint replacement, the said components have to be positioned in a defined way as precisely as possible with regard to their position and orientation in relation to the anatomy of the patient and the patient's body axes. Otherwise, an unsatisfactory result for the patient is to be expected. There are different surgical approaches with regard to the positioning of the components.

One approach which is known as mechanical alignment provides that the position and orientation of the artificial joint axes of the knee prosthesis are set in a mechanically ideal manner and to this extent without consideration of any orthopaedic misalignments of the patient. Here, the longitudinal axis of the tibia often serves as reference axis for the orientation and positioning. Clinical studies have shown that the mechanical alignment approach can lead to function of the artificial knee which is perceived to be unnatural.

A further approach is known as kinematic alignment. In this procedure, the femoral component and the tibial component are positioned with consideration of any orthopaedic misalignments of the patient. It is an aim here to re-establish the natural joint orientation, in some circumstances afflicted with misalignments, of the patient. Clinical studies have shown that the kinematic alignment approach is often accompanied by improved patient satisfaction. In particular, the function of the artificial knee is perceived by the patient as being rather natural.

The aim of further improving the patient satisfaction is accompanied by a fundamental requirement for surgical instruments which are as precise as possible, simple to use and cost-efficient for implementing the kinematic alignment. The present disclosure is concerned with a surgical instrument of this type and corresponding instrument systems.

Specifically, kinematic alignment provides that the distal femur cut is applied at a flexion/extension angle of 0°. Here, the distal femur cut is usually oriented orthogonally with respect to a metaphyseal anterior bone reference. Amongst experts, the flexion/extension angle usually describes a deviation with respect to the orthogonal orientation in relation to the said bone reference. The resection usually takes place by means of a cutting block which is attached to the distal femur and is also called a sawing block or cutting jig. In order for it to be possible for the femur cut to be applied with 0° flexion/extension, a corresponding orientation of the cutting block is required as a consequence. The orientation usually takes place by means of a reference block or a reference plate (alignment plate) which is applied with the use of an intra-medullary stem on the distal condyles of the femur. The intra-medullary stem is oriented parallel to the said bone reference. Before the distal femur cut is carried out, a check of the orientation of the cutting block is desirable.

SUMMARY

It is an object of the present disclosure to provide a surgical instrument which enables a simple and precise check of the orientation of the cutting block for the distal resection of the femur, and at the same time has as simple a construction as possible.

The surgical instrument according to the present disclosure comprises: a fastening device which is configured for direct or indirect releasable fastening to a cutting block for the distal resection of a femur, a sensing device with a posteriorly oriented reference plane which is configured to bear against an anterior surface of the femur, and a bearing device for positioning the reference plane, the bearing device having at least one pivoting bearing with an anteroposteriorly oriented pivot axis, about which the reference plane can be moved pivotably relative to the fastening device. By way of the solution according to the present disclosure, the reference plane of the sensing device can be moved rotationally about the pivot axis relative to the fastening device. In the use of the surgical instrument, this permits relative positioning of the reference plane in relation to the cutting block and therefore also in relation to the femur. As a result, positioning which is as precise as possible and, as a consequence, improved bearing of the reference plane against the anterior surface of the femur are made possible. The improved bearing permits a particularly simple and precise check of the orientation of the cutting block. In one embodiment, the fastening device is configured for direct (that is to say, immediate) fastening to the cutting block. The fastening device serves for releasable fastening of the surgical instrument. In a further embodiment, the fastening device is configured for indirect (that is to say, ancillary) fastening to the cutting block. In the last-mentioned case, the fastening device can be configured, for example, for direct fastening to a reference block, to which in turn the cutting block is fastened. In both cases, the fastening is releasable and can be configured, in particular, as a latched, plug-in, clamped and/or snap-in connection. The sensing device has the reference plane and serves for the actual check of the orientation of the cutting block. For this purpose, the reference plane is configured to bear against, i.e., to make contact with, said anterior surface of the femur which can also be called the anterior shield. In one embodiment, the reference plane is formed by way of a surface of a component and/or a portion of the sensing device. In a further embodiment, the reference plane is defined as it were by way of a plurality of portions of the sensing device. The reference plane is oriented posteriorly. In other words, the reference plane is plane-parallel to a frontal plane of the patient. The bearing device serves to position the reference plane in relation to the fastening device. For this purpose, the bearing device comprises at least the said pivoting bearing with the anteroposteriorly oriented pivot axis. The pivot axis and the reference plane are oriented orthogonally with respect to one another. In one embodiment of the present disclosure, the pivoting bearing is a separate component or a separate assembly which is connected firstly to the fastening device and secondly to the sensing device. In a further embodiment, the pivoting bearing is formed by way of components and/or portions of the fastening device and the sensing device.

The positional and directional designations used in this description relate to the body of a patient, in particular the patient's femur, and to this extent are to be understood in accordance with their customary anatomical meaning. As a consequence, "anterior" means front or lying at the front, "posterior" means rear or lying at the rear, "medial" means inner or lying on the inside, "lateral" means outer or lying on the outside, "proximal" means towards the body centre, and "distal" means away from the body centre. Furthermore, "proximodistal" means along, preferably parallel to, a proximal-distal axis, "anteroposterior" means along, preferably parallel to, an anterior-posterior axis, and "mediolateral" means along, preferably parallel to, a medial-lateral axis. Said axes are orthogonal with respect to one another, and it goes without saying that they can be understood in relation to X, Y and Z axes which are not associated with the anatomy of the patient. For example, the proximal-distal axis can as an alternative be called the X axis. The medial-lateral axis can be called the Y axis. The anterior-posterior axis can be called the Z axis. For improved illustration and for the sake of the simplicity of the designation, said anatomical positional and directional designations will primarily be used in the following text. Furthermore, designations such as "rear side" of a component or a portion of the surgical instrument, for example of the cutting block, are used in relation to a proximally directed viewing direction. In contrast, designations such as "front side" are used in relation to a distally directed viewing direction.

In one embodiment of the present disclosure, the bearing device has at least one first linear guide, by means of which the reference plane can be moved translationally relative to the fastening device along an anteroposteriorly oriented first bearing axis. As a result, a further degree of freedom is added to the relative movability of the reference plane, namely a translational degree of freedom along the first bearing axis. The first bearing axis is oriented anteroposteriorly and is therefore aligned parallel with respect to the pivot axis. In one embodiment, the first bearing axis is coaxial with respect to the pivot axis. The relative movability along the first bearing axis enables even more precise positioning of the reference plane and, as a consequence, once again improved bearing against the anterior surface of the femur. This permits a further improved check of the orientation of the cutting block. In one embodiment of the present disclosure, at least the reference plane can be moved along the first bearing axis. In a further embodiment, the entire sensing device can be moved along the first bearing axis.

In a further embodiment of the present disclosure, the bearing device has at least one second linear guide, by means of which the reference plane can be moved translationally relative to the fastening device along an at least predominantly proximodistally oriented second bearing axis. As a result, a further degree of freedom is added to the relative movability of the reference plane, namely a translational degree of freedom along the second bearing axis. The orientation of the second bearing axis is dependent on the respective pivoting position about the pivot axis, and is oriented at least predominantly proximodistally. As a result, the reference plane can be positioned at least predominantly in the longitudinal direction of the femur. This enables even more precise positioning and, as a consequence, further improved bearing against the anterior surface of the femur. The second bearing axis is oriented orthogonally with respect to the pivot axis. The second bearing axis is elongate in a plane which is oriented plane-parallel to the reference plane.

In a further embodiment of the present disclosure, the sensing device has a strut element which can be moved pivotably about the pivot axis and is elongate along its longitudinal direction between a first end and a second end, the reference plane being arranged or configured on a posteriorly oriented lower side of the strut element. The bearing device is preferably arranged at the second end of the strut element. The strut element protrudes at least predominantly proximally from the fastening device, the longitudinal direction of the strut element being oriented differently depending on a pivoting position about the pivot axis. If the surgical instrument has a first linear guide in accordance with one of the preceding embodiments, the entire strut element can be moved translationally along the first pivot axis in one embodiment. In a further embodiment, merely the reference plane can be moved translationally along the first bearing axis, the strut element otherwise being stationary in relation to the first bearing axis.

In a further embodiment of the present disclosure, the pivoting bearing has a pin receptacle and a complementary pin element which is mounted in the pin receptacle such that it can be moved pivotably about the pivot axis, the pin element being arranged at the second end of the strut element and the pin receptacle being arranged on the fastening device, or vice versa. The pin element engages into the pin receptacle axially along the pivot axis. The pin element and the pin receptacle interact slidably. In this embodiment, the pivoting bearing has a particularly simple and robust construction.

In a further embodiment of the present disclosure, the pin element is mounted in the pin receptacle such that it can be moved linearly along the pivot axis, preferably to a limited extent. As a result of the mounting of the pin element in a linearly movable manner to a limited extent, the strut element and therefore the reference plane can be moved translationally along the pivot axis, that is to say anteroposteriorly. In other words, in this embodiment, the pivoting bearing forms a first linear guide in accordance with one of the preceding embodiments. This embodiment enables relative positioning of the reference plane in relation to at least two degrees of freedom (about and along the pivot axis), a particularly simple construction of the surgical instrument being achieved or maintained at the same time.

In a further embodiment of the present disclosure, the strut element has a first strut portion which is elongate in a straight line starting from the second end and the posteriorly oriented lower side of which forms the reference plane, a second strut portion which is elongate starting from the first end in an anteriorly parallel offset manner with respect to the first strut portion, and a third strut portion which is at least predominantly anteroposteriorly elongate and connects the first strut portion and the second strut portion to one another. As a consequence, the strut element is angled-off in the broadest sense. The first strut portion is spaced apart posteriorly from the second strut portion. The second strut portion is spaced apart anteriorly from the first strut portion. The third strut portion is arranged between the first strut portion and the second strut portion in the longitudinal direction of the strut element.

In a further embodiment of the present disclosure, the sensing device has a slide element and a sensing element, the slide element being mounted on the strut element such that it can be moved linearly relative to the latter in the longitudinal direction of the strut element, the sensing element being mounted on the slide element such that it can be moved linearly relative to the slide element orthogonally with respect to the longitudinal direction of the strut element and/or anteroposteriorly, and the reference plane being arranged or configured at one end of the sensing element. This embodiment of the present disclosure enables particularly precise and variable positioning of the reference plane in relation to the fastening device. The slide element is mounted on the strut element such that it can be moved linearly along the latter. If the bearing device comprises a second linear guide in accordance with one of the preceding embodiments, the longitudinal direction of the strut element forms its second bearing axis. The sensing element and therefore the reference plane which is arranged or configured on it can be moved linearly relative to the slide element orthogonally with respect to the longitudinal direction of the strut element. As a consequence, the sensing element can be linearly moved anteroposteriorly. If the bearing device comprises a first linear guide in accordance with one of the preceding embodiments, the linearly movable mounting of the sensing element on the slide element forms its first bearing axis. The slide element can be moved relative to the strut element between the first end and the second end of the latter. The slide element is preferably guided on the strut element such that it can be moved slidingly. The sensing element is preferably guided on the slide element such that it can be moved slidingly.

In a further embodiment of the present disclosure, the sensing element is mounted on the slide element such that it can be rotated relative to the slide element about an anteroposteriorly oriented rotational axis. As a result, further improved positioning of the reference plane which is arranged or configured on the sensing element at one end can be achieved. The sensing element is preferably mounted on the slide element such that it can be moved linearly along the rotational axis.

In a further embodiment of the present disclosure, the fastening device is configured for direct releasable fastening to the cutting block and has a plug-in element which is elongate in a mediolaterally and anteroposteriorly planar manner and is configured to establish a positively locking and/or frictionally locking plug-in connection to a guide slot of the cutting block. In a state in which it is not plugged together with the plug-in element, the guide slot of the cutting block is configured for receiving and guiding a saw blade. In other words, the guide slot serves to guide the saw blade during the application of the distal femur cut. The plug-in element is configured for plugging into the said guide slot and is of complementary design with respect to the latter. As a result, particularly simple and nevertheless reliable releasable fastening of the surgical instrument to the cutting block is enabled. As a result of the direct fastening to the cutting block, its orientation can be checked particularly precisely and reliably.

In addition, the present disclosure relates to a surgical instrument system for use in a knee replacement operation, comprising a surgical instrument in accordance with one of the preceding embodiments and a cutting block for the distal resection of a femur, the cutting block having a guide slot which is arranged in a guide plane extending mediolaterally and anteroposteriorly for receiving and guiding a saw blade, the fastening device of the surgical instrument being directly or indirectly fastened to the cutting block, and the reference plane being oriented orthogonally with respect to the guide plane. The cutting block can also be called a femur cutting block (jig) or femur sawing block and is provided to guide the saw blade during the application of the distal femur cut. For this purpose, the cutting block has the said guide slot. The latter is planarly elongate in the guide plane. The guide plane is extended mediolaterally and anteroposteriorly. The fastening device is preferably fastened directly to the cutting block, preferably by means of the plug-in element in accordance with the preceding embodiment. The reference plane is oriented orthogonally with respect to the guide plane. As a result, the orientation usually used for the kinematic alignment with a flexion/extension angle of 0° can be checked particularly simply and precisely.

In a further embodiment of the present disclosure, there is a reference block which has a proximally oriented block rear side for bearing against distal condyles of the femur, the cutting block being fastened releasably to the reference block, and the guide plane being oriented in a plane-parallel manner and the reference plane being oriented orthogonally with respect to the block rear side. The proximally oriented block rear side serves for distal referencing of the reference block and therefore also of the cutting block which is fastened releasably to it. The guide plane of the cutting block is arranged in a plane-parallel and proximally offset manner with respect to the block rear side. The reference plane is oriented orthogonally with respect to the block rear side.

BRIEF DESCRIPTION OF THE DRAWING FIGURES

Further advantages and features of the present disclosure result from the following description of preferred exemplary embodiments of the present disclosure which are shown using the drawings.

DETAILED DESCRIPTION

Figure 1:
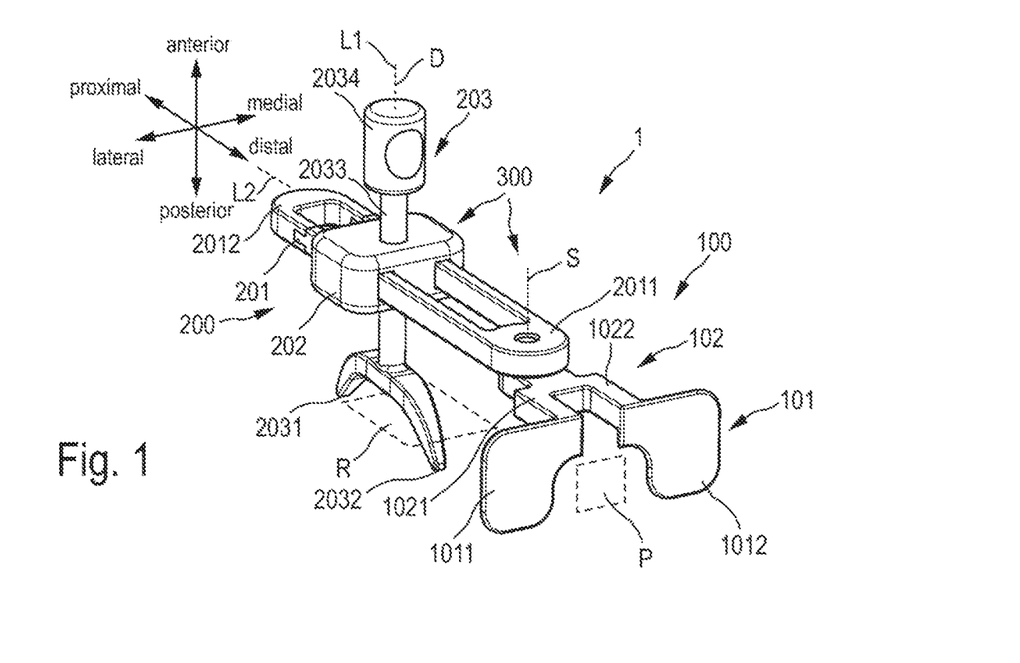
FIG. 1 shows a schematic perspective view of one embodiment of a surgical instrument according to the present disclosure.

According to FIG. 1, a surgical instrument 1 for use in a knee replacement operation is provided and comprises a fastening device 100, a sensing device 200 and a bearing device 300. The surgical instrument 1 is configured in a way which will still be described in greater detail for checking an orientation of a cutting block 400 for the distal resection of a femur F (see FIG. 3).

The fastening device 100 is configured for direct releasable fastening of the surgical instrument 1 to the cutting block 400.

The sensing device 200 has a posteriorly oriented reference plane R. The reference plane R is configured to check the orientation of the cutting block 400 on an anterior surface A of the femur F.

The bearing device 300 serves for improved positioning of the reference plane R in relation to the femur F. For this purpose, the bearing device 300 comprises at least one pivoting bearing with a pivot axis S. The pivot axis S is oriented orthogonally with respect to the reference plane R and/or anteroposteriorly. The reference plane R can be moved pivotably about the pivot axis S relative to the fastening device 100. In an intraoperative situation which will still be described in greater detail (see FIG. 3), the reference plane R can be oriented particularly precisely as a result relative to the anterior surface A of the femur F. This permits an improved check of the orientation of the cutting block 400.

Figure 2:
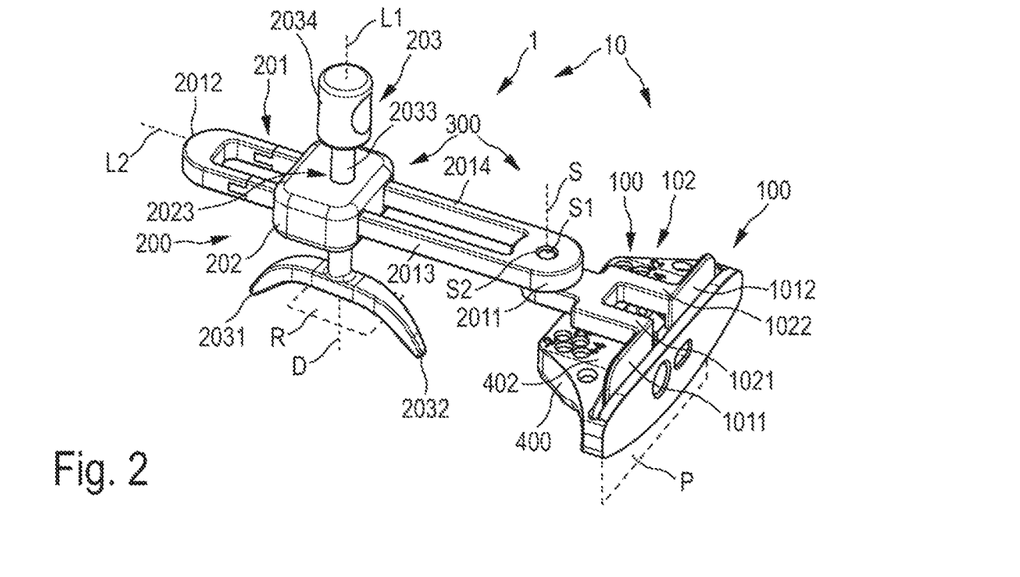
FIG. 2 shows a schematic perspective view of one embodiment of a surgical instrument system according to the present disclosure comprising the surgical instrument according to FIG. 1 and a femur cutting block.

In the present case, the surgical instrument 1 and the cutting block 400 form a surgical instrument system 10 (FIG. 2). In the present case, the instrument system 10 is a constituent part of a (superordinate) surgical instrument system 10' which, in addition to the surgical instrument 1 and the cutting block 400, comprises a reference block 500 and an intra-medullar stem 600. The interaction of the different components of the instrument system 10' and their specific function will be described in detail in the following text. First of all, the further construction of the surgical instrument 1 will be explained in greater detail.

In the present case, the bearing device 300 further comprises a first linear guide with a first bearing axis L1. The reference plane R can be moved translationally along the first bearing axis L1 relative to the fastening device 100. The first bearing axis L1 is oriented parallel to the pivot axis S and/or orthogonally with respect to the reference plane R.

In the embodiment which is shown, the bearing device 300 further comprises a second linear guide with a second bearing axis L2. The reference plane R can be moved translationally along the second bearing axis L2 relative to the fastening device 100. The second bearing axis L2 is oriented orthogonally with respect to the pivot axis S and/or orthogonally with respect to the first bearing axis L1.

In the present case, the reference plane R is moveable rotationally about the bearing axis L1.

In the embodiment which is shown, the bearing device 300 permits a relative movability of the reference plane R with a rotational degree of freedom about the pivot axis S, a translational degree of freedom along the bearing axis L1, a further translational degree of freedom along the second bearing axis L2, and a further rotational degree of freedom about the first bearing axis L1.

Figure 4:
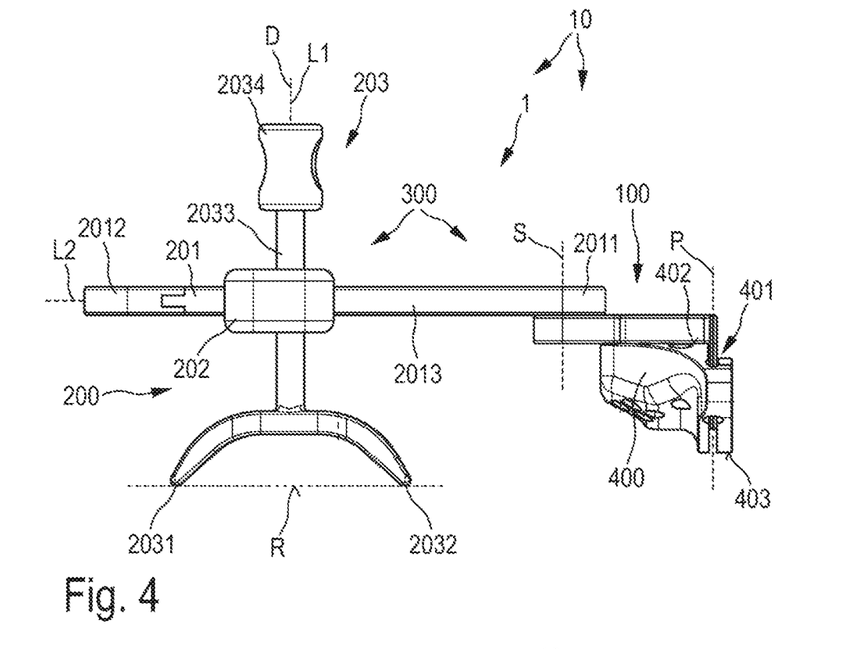
FIG. 4 shows the surgical instrument system according to FIG. 2 in a schematic side view with a medial viewing direction.
Figure 5:
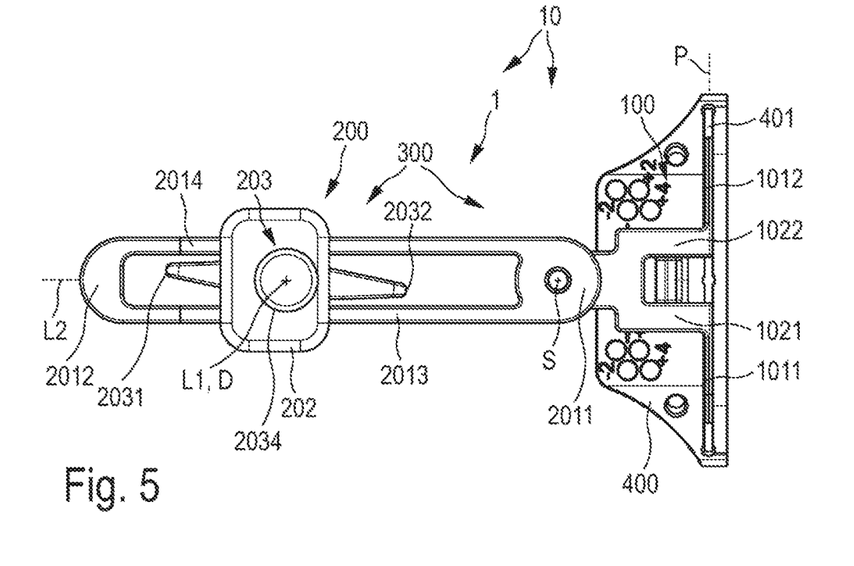
FIG. 5 shows the surgical instrument system according to FIGS. 2 and 4 in a schematic plan view with a posterior viewing direction.
Figure 6:
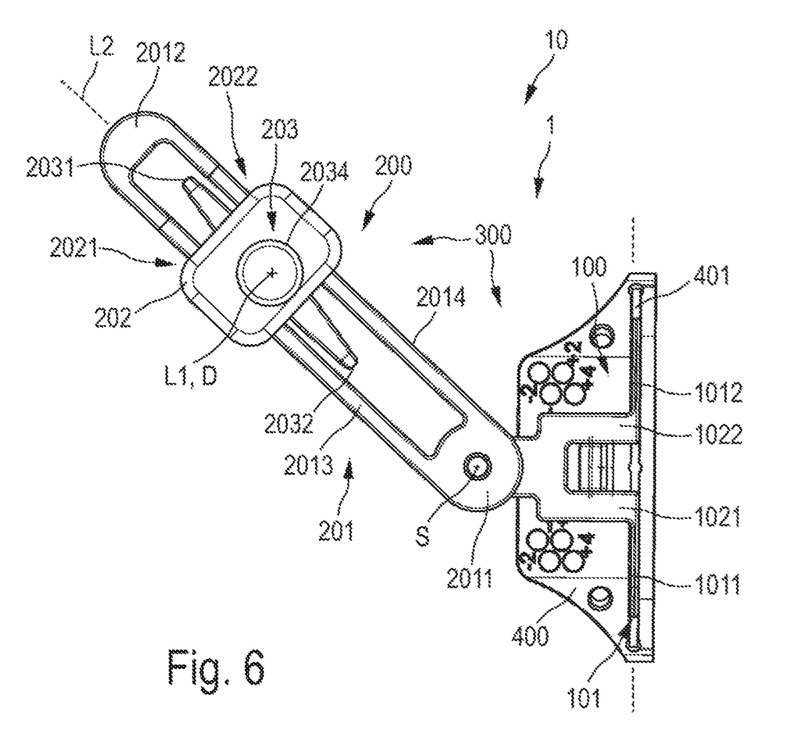
FIG. 6 shows a further schematic plan view according to FIG. 5, a sensing device of the surgical instrument being moved pivotably.

In the embodiment which is shown, the fastening device 100 is configured for direct releasable fastening to the cutting block 400 (see, in particular, FIG. 2). The cutting block 400 can also be called a sawing block or cutting jig. The cutting block 400 is provided to guide a saw blade during the application of a distal femur cut and, for this purpose, has a guide slot 401. The guide slot 401 is configured to receive and guide the saw blade, and reaches from a block upper side 402 as far as an opposite block lower side 403 (see, in particular, FIG. 4). The guide slot 401 defines a guide plane P, in which the said saw blade is guided during the application of the distal femur cut.

The fastening device 100 has a plug-in element 101 for releasable fastening to the cutting block 400. The plug-in element 101 is configured to establish a positively locking and/or frictionally locking plug-in connection to the guide slot 401. The plug-in element 101 is accordingly designed, dimensioned and/or configured so as to be complementary with respect to the guide slot 401. The plug-in element 101 is planar and extends in a plate-shaped manner. In a fastened state (FIGS. 2 to 6), the plug-in element 101 extends and/or is arranged in a coplanar manner in the guide plane P. The plug-in element 101 is oriented orthogonally with respect to the reference plane R.

In the embodiment which is shown, the plug-in element 101 has a lateral plug-in portion 1011 and a medial plug-in portion 1012. The two plug-in portions 1011, 1012 can also be called a lateral plate 1011 or lateral paddle 1011 and correspondingly a medial plate 1012 or medial paddle 1012.

Furthermore, in the embodiment which is shown, the fastening device 100 has a supporting element 102 which protrudes orthogonally from the plug-in element 101 in the direction of the sensing device 200 and the bearing device 300. In a fastened state of the surgical instrument 1, the supporting element 102 lies on the block upper side 402 of the cutting block 400 (FIG. 2). The supporting element is connected at one end to the plug-in element 101 and at the other end to the said pivoting bearing. In the present case, the supporting element 102 specifically has a lateral supporting portion 1021 and a medial supporting portion 1022. The lateral supporting portion 1021 is connected at one end to the lateral plug-in portion 1011. Accordingly, the medial supporting portion 1022 is connected at one end to the medial plug-in portion 1012.

In the embodiment which is shown, the sensing device 200 has a strut element 201 which can be moved pivotably about the pivot axis S. The strut element 201 is elongate along its longitudinal direction (without reference sign) between a first end 2011 and a second end 2012. The reference plane R is arranged and/or configured in a way which will be described in greater detail on a posteriorly oriented lower side of the strut element 201.

The pivot axis S is arranged in the region of the first end 2011 of the strut element 201 and, in the embodiment which is shown, has a pin element S1 and a pin receptacle S2. The pin element S1 engages into the pin receptacle S2 such that it can move slidingly about the pivot axis S. In the present case, the pin element S1 is arranged at one end of the fastening device 100. Specifically, the pin element S1 is arranged on the supporting element 102 at one end and so as to face away from the fastening element 101. The pin receptacle S2 is arranged at the first end 2011 of the strut element 201. In one embodiment (not shown in the drawings), the assignment of pin receptacle and pin element is reversed. To this extent, the pin element S1 can also be arranged on the strut element 201 and conversely the pin receptacle S2 can be arranged on the fastening device 100.

Furthermore, the sensing device 200 comprises a slide element 202 and a sensing element 203 in the present case. The slide element 202 can be moved translationally relative to the strut element 201 along the second bearing axis L2 (which coincides in the present case with the longitudinal axis of the strut element 201). For this purpose, the slide element 202 is mounted on the strut element 201 such that it can be moved slidingly.

In the present case, the strut element 201 has a lateral strut portion 2013 and a medial strut portion 2014. The two strut portions 2013, 2014 are elongate in each case between the first end 2011 and the second end 2012. The two strut portions 2013, 2014 are elongate parallel to one another. The slide element is guided on the strut portions 2013, 2014 such that it can be moved slidingly along the second bearing axis L2 and, for this purpose, has a lateral guide cut-out 2021 and a medial guide cut-out 2022. The two guide cut-outs 2021, 2022 extend in each case along the second bearing axis L2 continuously through the slide element 202. The lateral strut portion 2013 is received in the lateral guide cut-out 2021 such that it can be moved slidingly. The medial strut portion 2014 is received in the medial guide cut-out 2022 such that it can be moved slidingly. The slide element 202 can be moved along the second bearing axis L2 relative to the strut element 201 between a first end position and a second end position. In the first end position, the slide element 202 is arranged in the region of the first end 2011. In the second end position, the slide element 202 is arranged in the region of the second end 2012.

The sensing element 203 is mounted on the slide element 202 such that it can be linearly moved orthogonally with respect to the longitudinal direction of the strut element 201. In other words, the sensing element 203 is mounted on the slide element 202 such that it can be linearly moved along the first bearing axis L1 and/or orthogonally with respect to the second bearing axis L2 and/or orthogonally with respect to the reference plane R. The sensing element 203 configures the reference plane R at one end. For this purpose, at one end, the sensing element 203 has a sensing portion (without reference sign) with a first sensing tip 2031 and a second sensing tip 2032. The reference plane R extends between the two sensing tips 2031, 2032. Furthermore, the sensing element 203 has a shank portion 2033 and a grip portion 2034. The shank portion 2033 is connected at one end to the sensing portion (without reference sign) and at the other end to the grip portion 2034. The shank portion 2033 is guided in a guide bore 2023 of the slide element 202 such that it can be moved slidingly along the first bearing axis L1. In addition, in the present case, the shank portion 2033 is guided in the guide bore 2023 such that it can be moved rotationally about the first bearing axis L1. The grip portion 2034 is connected fixedly to the shank portion 2033 and, for example, can be gripped between the thumb and finger of a hand for the purpose of orientation of the reference plane R.

Figure 3:
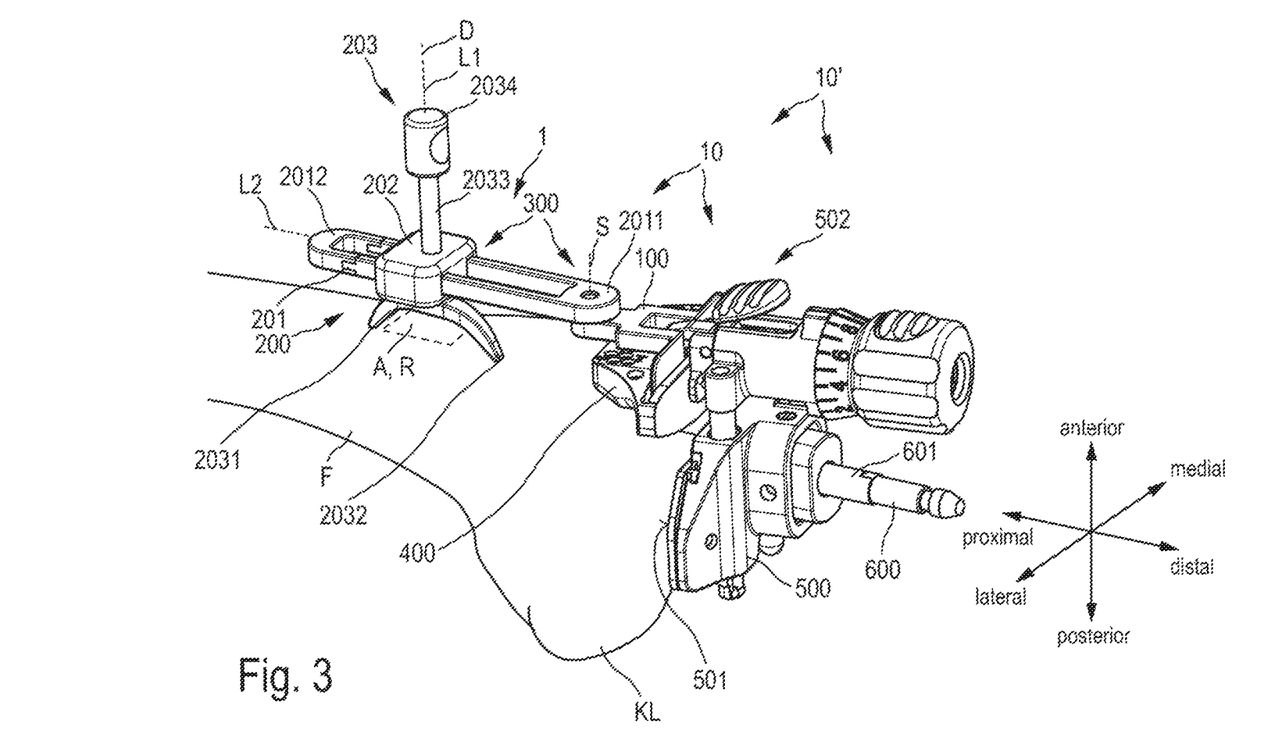
FIG. 3 shows a schematic perspective view of an intraoperative situation with use of the instrument system according to FIG. 2.

The further function of the surgical instrument 1 is explained in greater detail on the basis of FIG. 3 in conjunction with the surgical instrument system 10'. Here, FIG. 3 shows an intraoperative situation, in which the cutting block 400 is arranged distally and aligned on the femur F by means of the reference block 500. For this purpose, the reference block 500 is for its part pushed onto an intra-medullary stem 600 in a way which is fundamentally known to a person skilled in the art. The intra-medullary stem 600 is introduced in the proximal direction into the medullary cavity of the femur along a longitudinal axis (without reference sign) of the latter. The reference block 500 is pushed in the proximal direction onto a distal end 601 of the intra-medullary stem 600. Here, the reference block 500 has a proximally oriented block rear side 501. The proximal block rear side 501 is configured for bearing against the distal condyles of the femur F; merely the lateral distal condyle KL can be seen on the basis of FIG. 3. A perpendicular direction (without reference sign) of the block rear side 501 is elongate parallel to the proximodistal axis illustrated in FIG. 3, and points in the proximal direction.

The cutting block 400 is fixed releasably on the reference block 500 in a way which is known to a person skilled in the art. For this purpose, the reference block 500 comprises a fixing apparatus 502. Its specific construction and function are not essential to the present disclosure, with the result that further explanations in this regard can be dispensed with. In the present case, the reference block 400 is oriented in such a way that the guide plane P of the guide slot 401 is oriented plane-parallel to the block rear side 501. To this extent, the guide plane P extends in a mediolaterally and anteroposteriorly planar manner.

The surgical instrument 1 is fastened releasably to the cutting block 400 in order to check the orientation of the guide slot 401 and/or the guide plane P in the above-described way. For this purpose, said plug-in connection is established between the plug-in element 101 and the guide slot 401. The two plug-in portions 1011, 1012 are plugged posteriorly into the guide slot 401. The pivot axis S is oriented parallel to the anteroposterior axis illustrated in FIG. 3. This applies correspondingly to the first bearing axis L1. The second bearing axis L2 is oriented at least predominantly proximodistally, in a manner which is dependent on the pivoting position of the strut element 201 about the pivot axis S. The reference plane R is oriented orthogonally with respect to the block rear side 501.

In order to position the reference plane and/or the sensing tips 2031, 2032 in relation to the anterior surface A of the femur F, the sensing device 200 can be moved in the above-described way both about the pivot axis S and along the two bearing axes L1, L2. A translational movement along the first bearing axis L1 enables anteroposterior positioning of the reference plane R. A translational movement along the second bearing axis L2 enables proximodistal positioning of the reference plane R. In addition, the sensing portion (without reference sign) can be moved rotationally by means of a rotation of the sensing element 203 about the first bearing axis L1. This permits particularly precise positioning of the two sensing tips 2031, 2032 in relation to the anterior surface A.

There is an orientation of the cutting block 400 which meets the requirements, in particular, when the reference plane R coincides with the anterior surface A. In other words: there is an orientation which meets the requirements, in particular, when a reference axis which is projected onto the sagittal plane (within the reference plane R) coincides with a likewise projected osseous curve progression (within the anterior surface A).

After the orientation has been checked, the connection between the fastening device 100 and the cutting block 400 is released, and the surgical instrument 1 is removed. After this, the distal femur cut can be applied. For this purpose, said saw blade is introduced into the guide slot 401, and the distal condyles of the femur F are resected. Beforehand, the cutting block 400 is fixed on the femur F in a way which is known to a person skilled in the art.

Figure 7:
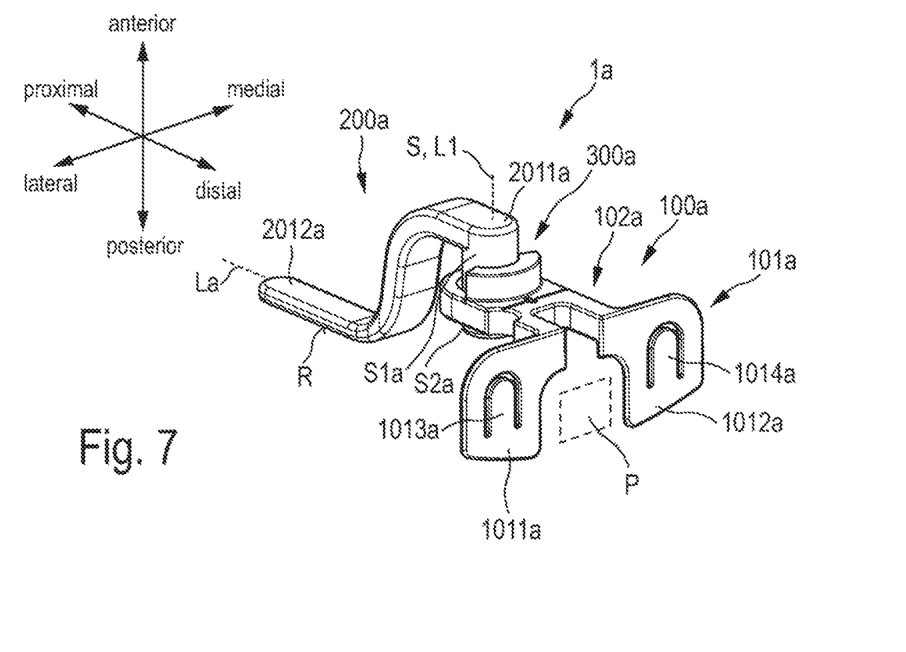
FIG. 7 shows a schematic perspective view of a further embodiment of a surgical instrument according to the present disclosure.
Figure 8:
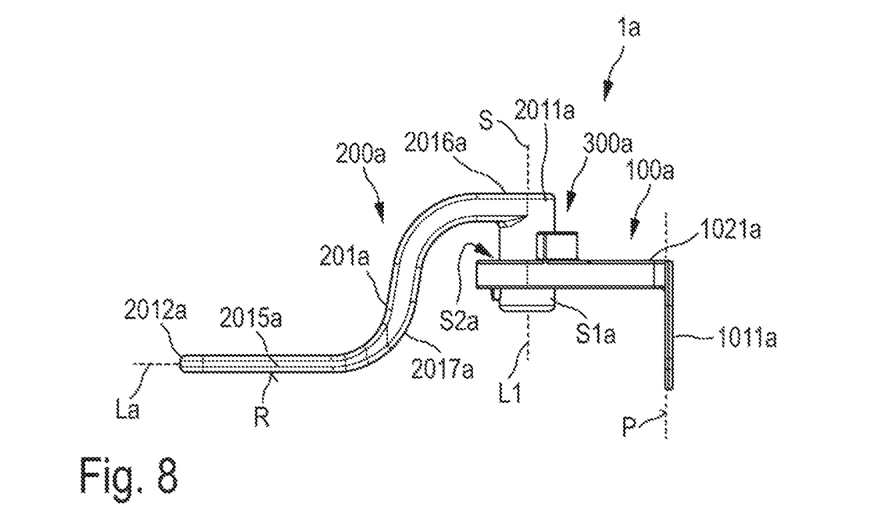
FIG. 8 shows the surgical instrument according to FIG. 7 in a schematic side view with a medial viewing direction.
Figure 9:
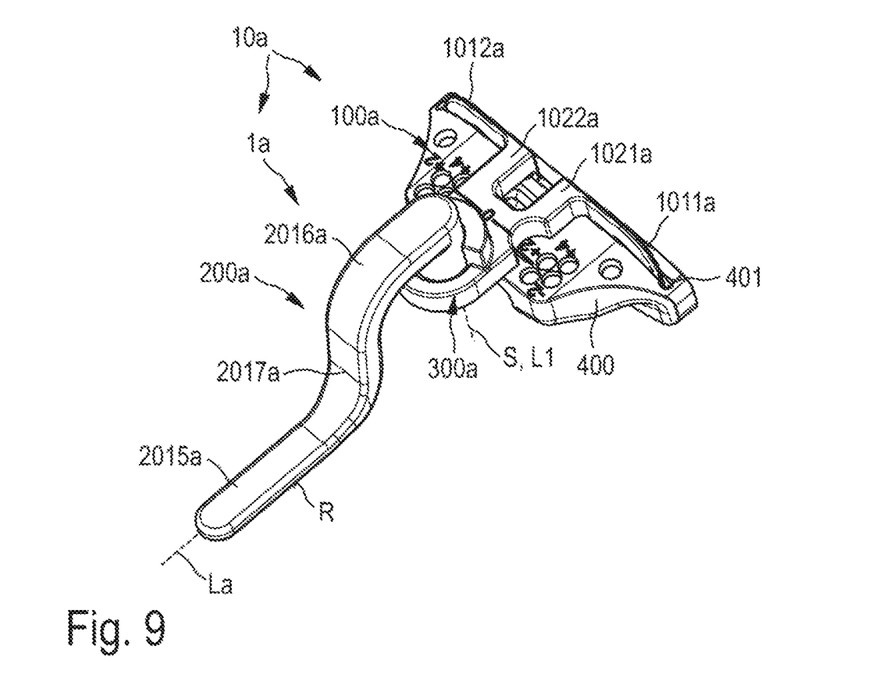
FIGS. 9 and 10 show schematic perspective views of a further embodiment of a surgical instrument system according to the present disclosure with a surgical instrument according to FIGS. 7 and 8 and a femur cutting block.
Figure 10:
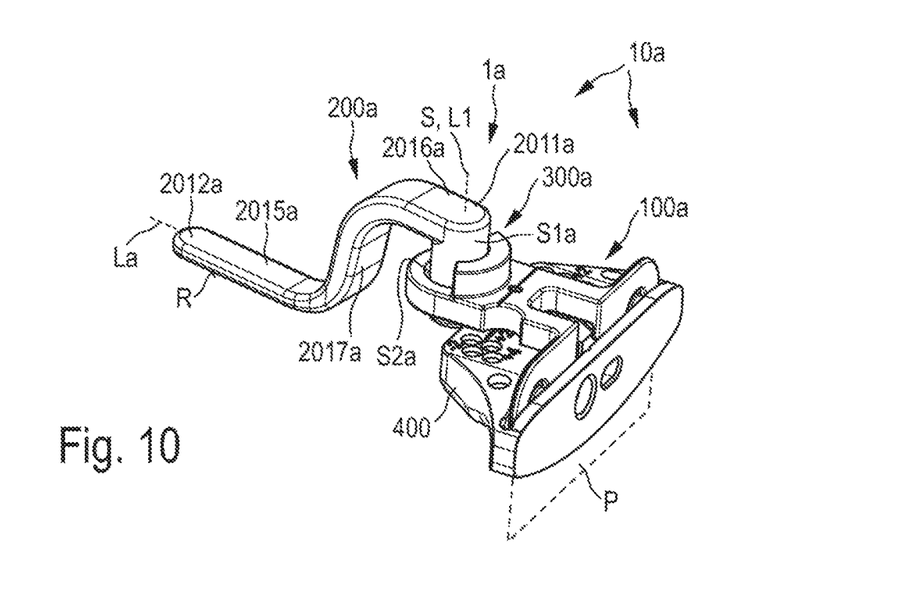
Figure 11:
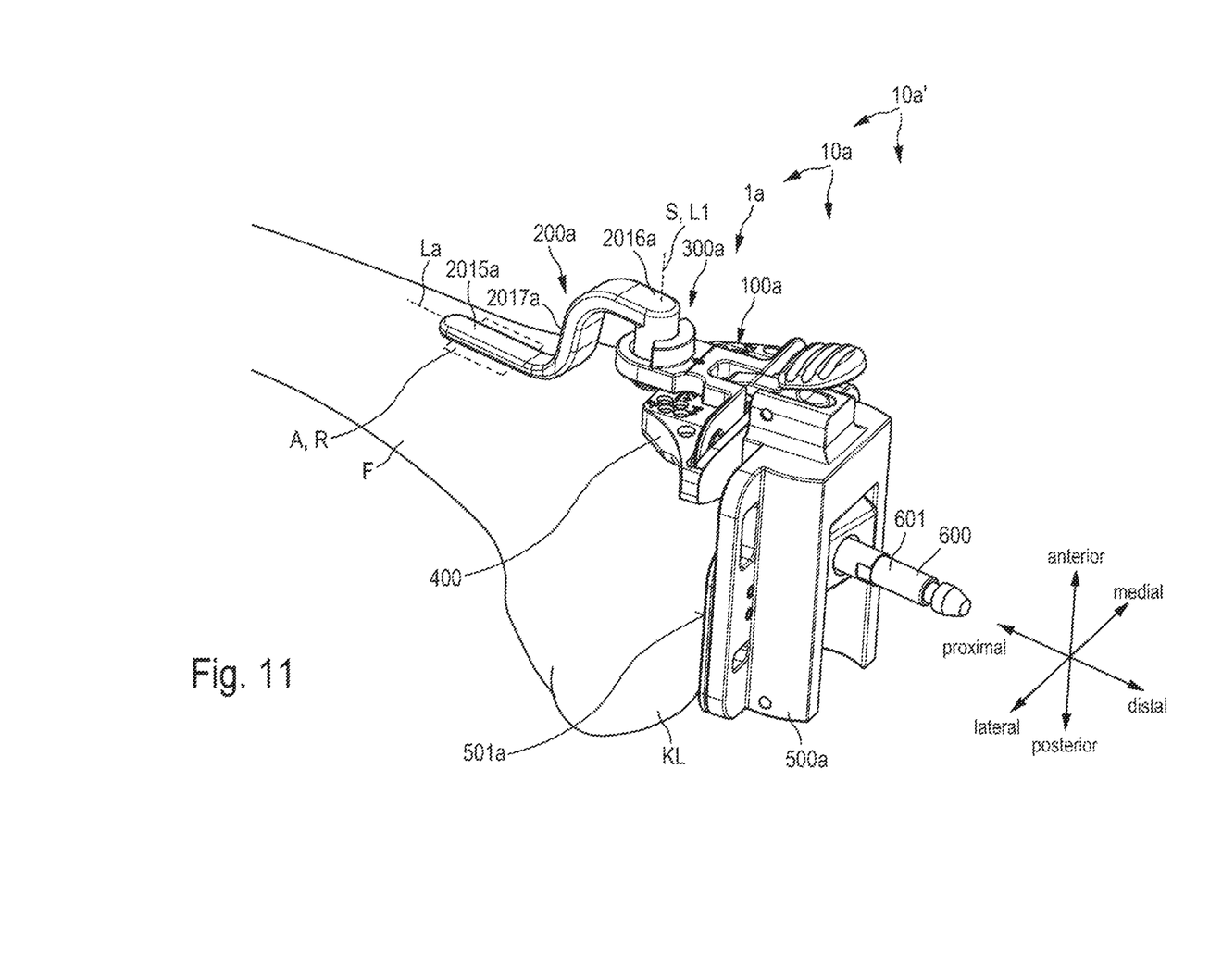
FIG. 11 shows a schematic perspective view of an intraoperative situation with use of the surgical instrument system according to FIGS. 9 and 10.

A further embodiment of a surgical instrument 1a according to the present disclosure is shown on the basis of FIGS. 7 and 8. FIGS. 9 and 10 show a further embodiment of a surgical instrument system 10a according to the present disclosure which comprises the surgical instrument 1a according to FIGS. 7 and 8 and the cutting block 400. Furthermore, FIG. 11 shows a further embodiment of a surgical instrument system 10a' according to the present disclosure which comprises the surgical instrument system 10a according to FIGS. 9 and 10 and additionally a reference block 500a and the intra-medullary stem 600. In order to avoid repetitions, merely essential differences of the surgical instrument 1a in comparison with the surgical instrument 1 according to FIG. 1 will be described in the following text. This applies, mutatis mutandis, to the surgical instrument systems 10a, 10a'. Substantially identical and functionally identical components and/or portions are not explained separately. Instead, reference is expressly made to and account is made of the disclosure with respect to the surgical instrument 1 and the surgical instrument systems 10, 10'.

The surgical instrument 1a differs from the surgical instrument 1 according to FIG. 1 primarily by way of a different design of the sensing device 200a and a design which is different in detail of the fastening device 100a.

The sensing device 200a once again comprises a strut element 201a. The strut element 201a is elongate along a longitudinal axis La between its first end 2011a and its second end 2012a. Here, the strut element 201a does not have a continuously straight longitudinal extent, but rather an angled-off longitudinal extent. The strut element 201a has a first strut portion 2015a, a second strut portion 2016a and a third strut portion 2017a.

Starting from the second end 2012a, the first strut portion 2015a extends rectilinearly along the longitudinal axis La. The first strut portion 2015a has a posteriorly oriented lower side (without reference sign) which forms the reference plane R (see FIG. 8, in particular). Starting from the first end 2011a, the second strut portion 2016a is elongate in parallel with and offset anteriorly from the first strut portion 2015a. In relation to the plane of the drawing of FIG. 8, the first strut portion 2015a is arranged below the second strut portion 2016a. The third strut portion 2017a is elongate at least predominantly orthogonally with respect to the longitudinal axis La and connects the first strut portion 2015a to the second strut portion 2016a.

In contrast to the reference plane of the surgical instrument 1 according to FIG. 1, the reference plane R in the present case cannot be moved translationally along the longitudinal axis of the strut element 201a.

Nevertheless, the strut element 201a is once again mounted on the fastening device 100a such that it can be moved pivotably about the pivot axis S. The pivot axis S is configured between a pin element S1a, configured on the strut element 201a in the region of the first end 2011a, and a pin receptacle S2a which is arranged on the fastening device 100a.

In conformity with the surgical instrument 1 according to FIG. 1, the bearing device 300a of the surgical instrument 1a has a first bearing axis L1. In contrast, the first bearing axis L1 in the present case coincides with the pivot axis S. The movability along the first bearing axis L1 follows from a linear displaceability between the pin element Sla and the pin receptacle S2a. In other words, the pin element S1a engages axially slidably into the pin receptacle S2a. In the present case, the linear displaceability between the pin element S1a and the pin receptacle S2a is limited by way of stops which are not denoted in greater detail. In the application of the surgical instrument 1a (see FIG. 11), a slidable translational movement of the pin element S1a in relation to the pin receptacle S2a permits setting of the reference plane R in relation to the anteroposterior axis which is shown in FIG. 11.

In further contrast to the surgical instrument 1 according to FIG. 1, the fastening device 100 (more precisely, the plug-in element 101a) in the present case comprises at least one spring tongue 1013a. In the embodiment which is shown, there are two spring tongues 1013a, 1014a which can also be called a lateral spring tongue 1013a and a medial spring tongue 1014a. The lateral spring tongue 1013a is arranged on the lateral plug-in portion 1011a. The medial spring tongue 1014a is arranged on the medial plug-in portion 1012a. The two spring tongues 1013a, 1014a are elastically resiliently movable in each case orthogonally with respect to the guide plane P. In a plugged-in state of the plug-in element 101a, the two spring tongues 1013a, 1014a press in each case in a manner which is loaded by spring force against an inner wall (without reference sign) of the guide slot 401. As a result, improved fastening is achieved.

Furthermore, it can be seen in relation to FIG. 11 that the reference block 500a there has a different design from the reference block 500 of the surgical instrument system 10'. The differences in this regard are not of significant importance with regard to the present disclosure. Further explanations in this regard are therefore superfluous.

The invention claimed is:

1. A surgical instrument for use in a knee replacement operation, comprising:
   a fastening device configured for direct or indirect releasable fastening to a cutting block for distal resection of a femur;
   a sensing device with a reference plane that is posteriorly oriented, the reference plane configured to bear against an anterior surface of the femur; and
   a bearing device for positioning the reference plane, the bearing device having at least one pivoting bearing with a pivot axis that is anteroposteriorly oriented, about which the reference plane is pivotably movable relative to the fastening device.

2. The surgical instrument according to claim 1, wherein the bearing device has at least one first linear guide, and the reference plane is translationally movable relative to the fastening device by the at least one first linear guide along a first bearing axis that is anteroposteriorly oriented.

3. The surgical instrument according to claim 1, wherein the bearing device has at least one second linear guide, and the reference plane is translationally movable relative to the fastening device by the at least one second linear guide along a second bearing axis that is at least predominantly proximodistally oriented.

4. The surgical instrument according to claim 1, wherein the sensing device comprises a strut element having a first end and a second end, the strut element being pivotably movable about the pivot axis and is elongate along a longitudinal direction of the strut element between the first end and the second end, the reference plane being arranged or configured on a lower side of the strut element that is posteriorly oriented.

5. The surgical instrument according to claim 4, wherein the at least one pivoting bearing has a pin receptacle and a pin element mounted in the pin receptacle such that the pin element is pivotably movable about the pivot axis, the pin element being arranged at the first end of the strut element and the pin receptacle being arranged on the fastening device, or vice versa.

6. The surgical instrument according to claim 5, wherein the pin element is mounted in the pin receptacle such that the pin element is linearly movable along the pivot axis.

7. The surgical instrument according to claim 4, wherein the strut element comprises:
- a first strut portion that is elongate in a straight line starting from the second end, the lower side of the first strut portion forming the reference plane;
- a second strut portion that is elongate starting from the first end in an anteriorly parallel offset manner with respect to the first strut portion; and
- a third strut portion that is at least predominantly anteroposteriorly elongate and connects the first strut portion and the second strut portion to one another.

8. The surgical instrument according to claim 4, wherein the sensing device has a slide element and a sensing element, the slide element being mounted on the strut element such that the slide element is linearly movable relative to the strut element in the longitudinal direction of the strut element, the sensing element being mounted on the slide element such that the sensing element is linearly movable relative to the slide element orthogonally with respect to the longitudinal direction of the strut element and/or anteroposteriorly, and the reference plane being arranged or configured at one end of the sensing element.

9. The surgical instrument according to claim 8, wherein the sensing element is mounted on the slide element such that the sensing element is rotatable relative to the slide element about a rotational axis that is anteroposteriorly oriented.

10. The surgical instrument according to claim 1, wherein the fastening device is configured for direct releasable fastening to the cutting block and has a plug-in element which is elongate in a mediolaterally and anteroposteriorly planar manner and is configured to establish a positively locking and/or frictionally locking plug-in connection to a guide slot of the cutting block.

11. A surgical instrument system for use in a knee replacement operation, comprising:
- the surgical instrument according to claim 1; and
- a cutting block for the distal resection of a femur,
- the cutting block having a guide slot arranged in a guide plane extending mediolaterally and anteroposteriorly for receiving and guiding a saw blade,
- the fastening device being directly or indirectly fastened releasably to the cutting block, and
- the reference plane being oriented orthogonally with respect to the guide plane.

12. The surgical instrument system according to claim 11, further comprising a reference block that has a block rear side that is proximally oriented for bearing against distal condyles of the femur, the cutting block being fastened releasably to the reference block, the guide plane being oriented in a plane-parallel manner, and the reference plane being oriented orthogonally with respect to the block rear side.

* * * * *